United States Patent [19]

Buysch et al.

[11] Patent Number: 5,218,135
[45] Date of Patent: Jun. 8, 1993

[54] PROCESS FOR THE PREPARATION OF DIALKYL CARBONATES

[75] Inventors: Hans-Josef Buysch; Alexander Klausener, both of Krefeld, Fed. Rep. of Germany

[73] Assignee: Bayer Aktiengesellschaft, Leverkusen, Fed. Rep. of Germany

[21] Appl. No.: 834,457

[22] Filed: Feb. 12, 1992

[30] Foreign Application Priority Data

Feb. 22, 1991 [DE] Fed. Rep. of Germany ....... 4105554

[51] Int. Cl.⁵ .................... C07C 68/00; C07C 68/06; C07C 69/96; C07C 29/09
[52] U.S. Cl. ...................................... 558/277; 568/867
[58] Field of Search ...................... 558/277; 568/867

[56] References Cited

U.S. PATENT DOCUMENTS 3,535,341  10/1970  Emmons et al. ............... 558/277 X
3,535,342  10/1970  Emmons ........................ 558/277 X
3,896,090  7/1975   Maximovich .................. 558/277 X
4,181,676  1/1980   Buysch et al. ................ 558/277 X
4,434,105  2/1984   Buysch et al. ................ 568/867 X

FOREIGN PATENT DOCUMENTS 0001777  5/1979  European Pat. Off. .
0069494  1/1983  European Pat. Off. .
0119840  9/1984  European Pat. Off. .
0522525  3/1988  European Pat. Off. .

Primary Examiner—Arthur C. Prescott
Attorney, Agent, or Firm—Sprung Horn Kramer & Woods

[57] ABSTRACT

A process for the preparation of dialkyl carbonates is described in which an alkylene carbonate is first formed from alkylene oxides and $CO_2$ and this alkylene carbonate is then transesterified with alkanols. Both reaction steps are carried out in the presence of a bifunctional catalyst of the formula $$[A_a-X_b]_m \cdot [B_c Y_d]_n \qquad (I)$$

wherein A, B, X, Y and the indices a, b, c, d, m and n have the meaning indicated in the description.

10 Claims, No Drawings

PROCESS FOR THE PREPARATION OF DIALKYL CARBONATES

The present invention relates to a process for the preparation of dialkyl carbonates from alkylene oxides, $CO_2$ and alkanols, wherein the associated alkylene carbonate is first formed in a first step and is then transesterified with the alkanol. The process is characterised by the use of the bifunctional catalyst described further below.

It is known to react alkylene oxides with $CO_2$ in the presence of catalysts to give alkylene carbonates. To this end, however, high temperatures and pressures are required in order to achieve industrially adequate rates of reaction. However, the use of these reaction conditions is problematical insofar as, on the one hand, the low molecular weight alkylene carbonates in particular claim industrial interest and, on the other hand, the alkylene oxides required as starting materials tend to decompose at these temperatures and pressures and therefore require safety devices. Moreover, a high expenditure on apparatus is generally required to control the temperatures and pressures. Catalysts which have been mentioned hitherto for carrying out the said reaction are, for example, the following: ammonium, phosphonium or sulphonium halides (DE-OS (German Published Specification) 3 244 456); a combination of protic compounds, such as alcohols, and nitrogen-containing bases (DE-OS (German Published Specification) 2 611 087)); arsonium halides (European Patent 180 387); phosphonium halides (U.S. Pat. 2,994,705); tertiary phosphines with alcohols (WO 84/03 701); and alkali metal transfer catalysts with crown ethers, diazabicyclooctene or tetramethylethylenediamine as complex ligands (Monatsh. Chem. 115 (1984), 205-214).

It is also known to transesterify alkylene carbonates with alcohols to give dialkyl carbonates. Thus, according to DE-OS (German Published Specification) 2 740 243), high yields of dimethyl carbonate or diethyl carbonate are obtained from the reaction of ethylene carbonate or propylene carbonate with methanol or ethanol in the presence of alkali metal compounds. Temperatures of about 150°-200° C. and the associated pressures are required in this reaction. At lower temperatures unusably long transesterification times result.

In the process of DE-OS (German Published Specification) 2 740 251, in which the reaction is carried out in the presence of thallium compounds, high yields are also achievable only at high temperatures and the associated pressures.

Furthermore, it is known to obtain the alkyl carbonates directly from alkylene oxides, $CO_2$ and alcohols (European Patent 1777). In this case also, high temperatures and associated high pressures must be used. Moreover, glycol ethers are obtained as by-products and have to be separated off in a separate distillation.

In Chem. Ber. 119 (1986), 1090-1094 it is proposed to carry out the reaction of an alkylene oxide (oxirane) with $CO_2$ at normal pressure and room temperature. To this end the solution of a catalyst in an alkylene oxide is saturated with $CO_2$. If, in accordance with this proposal, bifunctional catalysts which consist of metal dichlorides acting as Lewis acids and onium iodides or bromides are used, in some cases considerable yields of alkylene oxides are obtained under the indicated mild conditions. However, the reaction times are in general very long. In addition to this disadvantage of the long reaction time and of the yield, which is inadequate in most cases, it is impossible, because of the safety risk on an industrial scale, to handle large amounts of alkylene oxide in the presence of catalysts. Accordingly, this proposal is in several respects in sharp contrast to the processes mentioned above, in which yields of about 99% are frequently obtained at the said high temperatures and high pressures.

For transesterification of the alkylene carbonates, obtained in accordance with the processes described, with alcohols, the catalyst contained in the alkylene carbonates must as a rule be removed, which is frequently effected by distilling off the alkylene carbonates from the catalyst residues. The residual catalysts can as a rule be re-used. Some of the catalysts proposed for the formation of alkylene carbonate, such as, for example, the quaternary ammonium salts, have also been employed as transesterification catalysts; the transesterification rates achieved are, however, unsatisfactory.

Accordingly, to date there is no industrial process which allows the synthesis of alkylene carbonate from alkylene oxide and carbon dioxide to be carried out under conditions which are still usable industrially, high to virtually quantitative conversions and likewise virtually quantitative yields of alkylene carbonates being achieved at the same time, and with which a direct further reaction to give the desired dialkyl carbonates by transesterification with alkanols takes place, it being possible, in a preferred manner, to dispense with an isolation and intermediate purification of the alkylene carbonates, and with which high conversions and selectivities in respect of the ultimately desired dialkyl carbonates are also achieved in this second (transesterification) step.

It has now been found that both reaction steps, that is to say the formation of the alkylene carbonate and the subsequent transesterification, can advantageously be carried out in the presence of the bifunctional catalyst of the formula (I) described further below, it being possible to operate at industrially suitable temperatures of 40°-190° C. and pressures below 10 bar and the two reaction steps according to the invention being advantageously influenced by the same catalyst system.

This is surprising because, according to Chem. Ber. 123 (1990), 277-283, the reaction of $CO_2$ with alkylene oxides in the presence of bifunctional catalysts already becomes retrogressive at temperatures above 50° C. and splitting of the alkylene carbonates into $CO_2$, alkylene oxides and aldehydes thus starts (loc cit., p. 278, left-hand column, paragraph 2).

The process according to the invention is furthermore surprising in that the transesterification of the alkylene carbonates, formed as intermediates, with alcohols in the presence of the same bifunctional catalysts of the formula (I) already proceeds rapidly and smoothly under mild conditions which can also used industrially, whereas the individual constituents of these bifunctional catalysts make the transesterification possible only slowly and thus at a rate which is industrially unsatisfactory. Even the mixtures of the individual components of the bifunctional catalysts have an inadequate effect in the transesterification step if they have not previously been used according to the invention to form the alkylene carbonates. The bifunctional catalysts of the formula (I) accordingly undergo a surprising increase in their catalytic activity for the transesterification according to the second step of the process according to the invention as a result of their use in the first step of the process according to the invention.

The invention accordingly relates to a process for the preparation of dialkyl carbonates from alkylene oxides, $CO_2$ and alkanols in the presence of a catalyst, which is characterised in that, in a first step, an alkylene oxide having 2-8 C atoms is reacted with $CO_2$ in the alkylene carbonate which is to be formed first as reaction medium, at 40°-190° C., preferably at 50°-170° C. and particularly preferably below 8 bar, particularly preferentially below 5 bar and very particularly preferentially below 3 bar, and, in a second step, the alkylene carbonate thus formed is transesterified with a (cycl)aliphatic $C_1-C_{10}$ monohydroxy compound, which can be substituted by $C_3-C_6$ cycloalkyl or phenyl, at 50°-160° C., preferably at 60°-150° C. and particularly preferentially at 70°-140° C., and under the autogenous pressure, both steps being carried out in the presence of a bifunctional catalyst of the formula $$[A_a-X_b]_m \cdot [B_c Y_d]_n \qquad (I)$$

wherein

A is the cation of a metal which belongs to the third period and Group IIa, the fourth period and Group IIa, IVa - VIIIa, IB or IIb, the fifth period and Group IIa, IVa - VIIa, IIb or IVb, or the sixth period and Group IIa VIa of the Periodic System of the elements in the short period form, X is the anion of an inorganic or organic acid, B represents a cation from the group comprising the alkali metal or alkaline earth metal cations, the quaternary ammonium, phosphonium, arsonium or stibonium ions and the ternary sulphonium cations, Y is a halide ion, preferably bromide or iodide, particularly preferentially iodide, it being possible for X and Y to change positions if at least one of the anions is bromide or iodide, a and b independently of one another represent integers from 1 to 5 and c and d independently of one another represent integers from 1 to 3, the requirements in respect of the valencies of the cations and anions for the formation of a neutral salt having to be met, and m and n independently of one another assume values of 0.001-1.

The process according to the invention is described for the formation of dimethyl carbonate from ethylene oxide, $CO_2$ and methanol by the following equation:

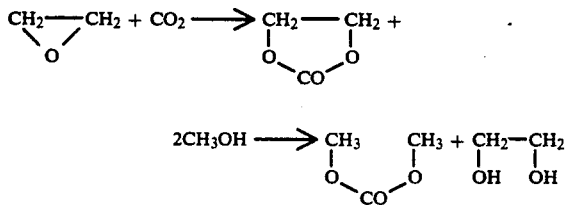

Alkylene oxides having 2-8 C atoms are, preferably, those of the formula:

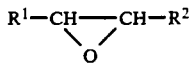

wherein $R^1$ denotes hydrogen, straight-chain or branched $C_1-C_6$ alkyl, straight-chain or branched $C_2-C_6$ alkenyl or chlorine and $R^2$ denotes hydrogen or $C_1-C_3$ alkyl, it being possible for $R^1$ and $R^2$ together also to represent trimethylene, tetramethylene or pentamethylene and the total number of C atoms not exceeding 8.

Particularly preferentially, the alkylene oxide employed is ethylene oxide, propylene oxide, 1,2- or 2,3-butylene oxide, cyclohexene oxide, vinyloxirane or epichlorohydrin, particularly preferentially ethylene oxide or propylene oxide.

The following may be mentioned as (cyclo)aliphatic $C_1-C_{10}$ monohydroxy compound, which can be substituted by $C_3-C_6$ cycloalkyl or phenyl: a straight-chain or branched $C_1-C_{10}$ alkanol or a $C_3-C_8$ cycloalkanol. In both cases a $C_3-C_6$ cycloalkyl or phenyl substituent can be present. Examples of such monohydroxy compounds are: methanol, ethanol, propanol, isopropanol, butanol, isobutanol, amyl alcohol, hexyl alkanol, octyl alkanol, decyl alkanol, cyclopropyl alkanol, cyclopentyl alkanol, cyclohexanol, methylcyclohexanol and dimethylcyclohexanol, cyclohexanemethanol and benzyl alcohol; preferably, straight-chain or branched $C_1-C_4$ alkanol of the indicated type, particularly preferentially methanol and ethanol, may be mentioned.

The $CO_2$ to be employed according to the invention can be contaminated by inert gases, such as nitrogen, hydrogen, carbon monoxide or lower hydrocarbons, and can originate from natural sources or from industrial off-gases.

The molar ratio of the reactants alkylene oxide and $CO_2$ in the first reaction step is as a rule approximately 1:1. However, it is also possible to use an excess of $CO_2$, which in principle is not critical but for economic considerations should be restricted and is rarely more than twice the required amount.

In the case of the transesterification reaction (2nd process step), the molar ratio of alcohol to alkylene carbonate present is variable within wide limits and can be from 1:1 to 1:100, preferably from 1:2 to 1:50, particularly preferentially 1:2 to 1:30 and very particularly preferentially from 1:2 to 1:20. For economic reasons, however, a ratio of 1:1 to 1:20 is preferred.

The process according to the invention is characterised in particular by the use of the bifunctional catalysts of the formula (I). In these bifunctional catalysts, the molar ratio of the two components in square brackets is expressed by the indices m and n. These indices can independently of one another assume values of 0.001 to 1, preferably of 0.01 to 1, particularly preferentially of 0.05 to 1 and very particularly preferentially of 0.1 to 1. Neutral salts consisting of one cation and one anion are inside the square brackets. The indices a and b independently of one another represent integers from 1 to 5; the indices c and d independently of one another integers from 1 to 3, the requirements in respect of the valencies of the cations and anions for the formation of such neutral salts having to be met.

A is the cation of a metal which to the third period and Group IIa, the fourth period and Group IIa, IVa - VIIIa, Ib or IIb, the fifth period and Group IIa, IVa - VIIa, IIb or IVb and the sixth period and Group IIa - VIa of the Periodic System of the elements in the short period form to.

Those skilled in the art take the metals suitable for the cation A from the customer representations of the Periodic System of the elements (Mendelejew). Preferentially, A is the cation of one of the metals Mg, Ca, Sr, Ba, Zn, Cu, Mn, Co, Ni, Fe, Cr, Mo, W, Ti, Zr, Sn, Hf, V and Ta and particularly preferentially the cation of one of the metals Mg, Ca, Zn, Co, Ni, Mn, Cu and Sn. Apart from the non-complexed cations of the said metals, cationic oxo complexes of the said metals are also suitable, such as, for example, titanyl $TiO^{++}$ and chromyl $CrO_2^{++}$.

The anion X associated with the cation A is the anion of an inorganic or organic acid. An inorganic or organic acid of this type can be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1-16 C atoms and benzoate; examples of anions of dibasic inorganic or organic acids are: sulphate, oxalate, succinate, fumarate, maleate, phthalate and others; examples of tribasic inorganic or organic anions are: phosphate or citrate. Preferred anions X in the catalyst of the formula (I) are: fluoride, chloride, bromide, iodide, sulphate, nitrate, phosphate, formate, acetate, propionate, oxalate, butyrate, citrate, succinate, fumarate, maleate, benzoate, phthalate, decanoate, stearate, palmitate and laurate. Particularly preferred anions X are: chloride, bromide, iodide, acetate, laurate, stearate, palmitate, decanoate, nitrate or sulphate.

Cation B in the catalysts of the formula (I) can be a cation from the group comprising the alkali metal or alkaline earth metal cations, the quaternary ammonium, phosphonium, arsonium or stibonium cations and the ternary sulphonium cations.

Alkali (alkaline earth) metal cations which may be mentioned are: the lithium, sodium, potassium, rubidium, caesium, magnesium, calcium, strontium and barium cation, preferably the alkali metal cations mentioned and particularly preferentially the sodium cation and the potassium cation.

Preferentially, cation B can be cations of the formulae

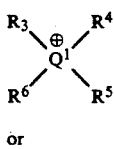

(III)

or

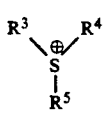

(IV)

wherein $Q^1$ represents N, P, As or Sb and $R^3$, $R^4$, $R^5$ and $R^6$ independently of one another are straight-chain or branched $C_1$–$C_{18}$ alkyl or $C_7$–$C_{12}$ aralkyl and one of the radicals $R^3$ to $R^6$ can also be $C_6$–$C_{12}$ aryl.

Particularly preferentially, B is a cation of the formula

(V)

wherein $Q^2$ represents N or P, preferably N.

Very particularly preferentially, the radicals $R^{13}$, $R^{14}$, $R^{15}$ and $R^{16}$, which independently of one another denote straight-chain or branched $C_1$–$C_{12}$ alkyl or $C_7$–$C_8$ aralkyl, are present in place of the radicals $R^3$, $R^4$, $R^5$ and $R^6$ respectively within the framework of the formula (III) or (V) and one of the radicals $R^{13}$ to $R^{16}$ can also be phenyl. In a further very particularly preferred manner, the radicals $R^{23}$, $R^{24}$, $R^{25}$ and $R^{26}$, which independently of one another denote $C_1$–$C_8$ alkyl or benzyl, are present in place of the radicals $R^{13}$, $R^{14}$, $R^{15}$ and $R^{16}$ respectively and one of the radicals $R^{23}$ to $R^{26}$ can also be phenyl.

Straight-chain or branched $C_1$–$C_{18}$ alkyl is, for example, methyl, ethyl, propyl, isopropyl, butyl, isobutyl, hexyl, octyl, dodecyl, hexadecyl or octadecyl.

$C_7$–$C_{12}$ aralkyl is, for example, benzyl, phenylethyl, phenylpropyl, naphthylmethyl or naphthylethyl; preferred aralkyl is benzyl or phenylethyl and very particularly preferred aralkyl is benzyl.

Preferred alkyl has 1-12 C atoms and particularly preferred alkyl has 1-8 C atoms.

The anion Y in the catalyst of the formula (I) is a halide ion, such as fluoride, chloride, bromide or iodide, preferably bromide or iodide and particularly preferentially iodide. However, it can also have the meaning of other anions mentioned under X if, in the specific case, the anion X is bromide or iodide.

The bifunctional catalyst of the formula (I) is employed in the first step in an amount of 0.005-10% by weight, preferably 0.1-5% by weight and particularly preferentially 0.02-3% by weight, based on the alkylene carbonate initially introduced. It is employed in the second step in an amount of 0.005-5% by weight, preferably 0.01-3% by weight and particularly preferentially 0.01-1% by weight, based on the total transesterification mixture.

The reaction temperature is 40°-190° C., preferably 50°-170° C. and particularly preferentially 60°-160° C. in the first step and 50°-160° C., preferably 60°-150° C. and particularly preferentially 70°-140° C. in the second step.

The first step is carried out under a pressure of below 10 bar, preferably below 8 bar, particularly preferentially below 5 bar and very particularly preferentially below 3 bar. The lower limit for the pressure for the first reaction step is approximately 1 bar. The second step is generally carried out under the autogenous pressure which is established and which is essentially determined by the boiling point of the transesterification alcohol used under the particular conditions. Adjustment to a higher pressure brings no further advantages, but is also not detrimental for carrying out the process according to the invention.

The reaction in the first step of the process according to the invention is carried out in the particular alkylene glycol carbonate which is formed in this reaction step, that is to say in ethylene glycol carbonate if ethylene oxide is reacted with $CO_2$ and in propylene glycol carbonate if propylene oxide is reacted with $CO_2$. The amount of the particular alkylene carbonate is to be regulated such that rapid absorption and reaction of the reactants is ensured. This amount can be determined by means of preliminary experiments and in general at least equals the amount of the amount of alkylene carbonate to be produced per hour in the reaction vessel.

The second reaction step can, in principle, be carried out in such a way that the alkylene carbonate formed is separated off and purified and is then reacted in the presence of a catalyst of the formula (I) with the alcohol which is desired as ester component. The catalyst of the formula (I) for the second reaction step can be that from the first reaction step or a different catalyst which falls under the formula (I) and which has likewise already been used once for the reaction in the first step. Preferentially, however, the reaction mixture from the first step is not subjected to particular working up or purification but is fed immediately to the transesterification with the addition of the (cyclo)aliphatic $C_1$–$C_{10}$ monohydroxy compound.

The reaction in the first step can be carried out in conventional reaction vessels which are designed for the indicated pressure and have a stirrer device. The reactants are metered in by injection or by pumping in, in the manner familiar to those skilled in the art. The $CO_2$ and, insofar as the alkylene oxides are vapourisable, the alkylene oxide vapours are preferably metered in with the aid of gassification stirrers, frits or similar devices which ensure rapid and uniform distribution of these reactants, as a result of which, in turn, absorption and rapid reaction are ensured. If the reaction is carried out discontinuously it is possible, for example, initially to introduce an amount of alkylene carbonate and the above-described amount of bifunctional catalyst and then to continue the reaction by adding alkylene oxide and $CO_2$ until the reaction vessel is filled. For semi-continuous or continuous operation of the reaction, however, it is also possible to withdraw reaction mixture from the reaction vessel in accordance with the amount of alkylene carbonate freshly formed, this withdrawal being carried out continuously or batch-wise. In the case of such a reaction variant, bifunctional catalyst of the formula (I) is correspondingly added to the reaction vessel so that the reaction mixture does not become depleted in catalyst. In a corresponding manner, it is further possible to carry out the withdrawal of the freshly formed alkylene carbonate only from a second or further reactor in which a post-reaction has taken place.

A further, particularly preferred embodiment of the alkylene carbonate synthesis (first step of the process according to the invention) uses a bubble column as reaction vessel, into which the gaseous components are injected from below via a gas distributor, as described above, and liquid components are injected through conventional metering devices. A rapid and complete reaction of the reactants is achieved in simple reaction vessels in this way. A bubble column of this type is a typical reaction vessel for carrying out a process in continuous operation.

The transesterification can also take place in conventional reactors, such as stirred vessels, autoclaves, tubular reactors and tube bundle reactors, which can also be combined to give cascades for continuous operation. In the case of continuous operation, the transesterification is preferably carried out in tubular reactors, in which a back-mixing can be substantially eliminated, so that at the end of the reactor the transesterification equilibrium is established and as high as possible a transesterification rate is achieved. Trickle phase, in which the alkyl carbonate is fed over packing in a column as a trickle counter-current to the stream of oxirane and $CO_2$, offers a further possibility for the transesterification.

The mixture obtained from the transesterification is preferably worked up by distillation. By means of this procedure any excess (cyclo)aliphatic monohydroxy compound and the obtaining carbonate of this monohydroxy compound can be obtained by fractionation. The catalyst remaining as residue can preferably by recycled into the first reaction step. If a less than stoichiometric amount of monohydroxy compound had been used for the transesterification, the catalyst remains behind in excess alkylene carbonate following working up by distillation. With this procedure also, the catalyst can be recycled into the first step, the alkylene carbonate present at the same time constituting the reaction medium to be used according to the invention.

EXAMPLE 1–12

A 500 ml three-necked flask fitted with a stirrer, thermometer and gas inlet tube was charged with 200 g of ethylene glycol carbonate and with catalyst in accordance with the following table and heated to 50° and a gentle stream of ethylene oxide and carbon dioxide gas was introduced with stirring. After 4 h in each case, the contents of the flask were weighed and the increase in weight determined. In every case, analysis of the reaction product by gas chromatography showed that no by-products had formed during the reaction.

TABLE

| | (Examples 1–12) | | |
|---|---|---|---|
| | Catalyst | | Increase in |
| No. | 1.4 g | 0.5 g | weight g |
| 1 | $NBu_4I$[1] | $ZnCl_2$ | 13 |
| 2 | " | $MgCl_2$ | 11 |
| 3 | " | $CaCl_2$ | 9 |
| 4 | " | $CuCl_2$ | 12 |
| 5 | " | $Cu(OAc)_2$[2] | 11 |
| 6 | " | $SnCl_2$ | 11 |
| 7 | " | $NiCl_2$ | 10 |
| 8 | " | $CoCl_2$ | 19 |
| 9 | " | $Sn(OLau)_2$[3] | 10 |
| 10 | " | $Zn(OAc)_2$ | 9 |
| 11 | KI | $ZnCl_2$ | 12 |
| 12 | [4] | [4] | 13 |

[1] $NBu_4I$ = tetrabutylammonium iodide
[2] OAc = acetate
[3] OLau = laurate
[4] catalyst = residue from Example 1 after distillation of the reaction mixture obtained from the subsequent transesterification

EXAMPLE 13

In a 500 ml three-necked flask fitted with a stirrer, thermometer and gas inlet tube, 330 g of ethylene glycol carbonate, in which 5 g of $NBu_4I$ and 1.25 g of $ZnCl_2$ had been dissolved, were treated at 50°, with vigorous stirring, over a period of 6 hours with a total of 1 mol of gaseous ethylene oxide and 1 mol of gaseous carbon dioxide. The increase in weight was 60 g. By-products were not detected.

EXAMPLE 14

700 g of ethylene glycol carbonate, which contained 10 g of tetrabutylammonium iodide and 2.5 g of zinc chloride, were heated to 80° in a vertical tube 130 cm long and 3.0 cm in diameter, which was provided with a heating jacket and with a frit at the bottom, and a total of 70 g of gaseous carbon dioxide and 70 g of gaseous ethylene oxide were introduced through the frit over a period of 6 h. The gas mixture was converted virtually completely to glycol carbonate in the bubble column. The increase in weight was accordingly 139 g.

EXAMPLE 15

Example 14 was repeated, 5 g instead of 10 g of tetrabutylammonium iodide and 1.25 g instead of 2.5 g of zinc chloride being used and the reaction mixture being kept at 100°. In total 50 g of carbon dioxide and 50 g of ethylene oxide were introduced through the frit over a period of 3½ h. The absorption of the gas mixture and thus the reaction and the conversion to ethylene glycol carbonate were virtually complete. The increase in weight at the end of the reaction was 99 g.

COMPARISON EXAMPLE 1

Example 14 was repeated, only 5 g of tetrabutylammonium iodide being used instead of the catalyst mixture of tetrabutylammonium iodide and zinc chloride. The treatment with gas was carried out using a gas mixture consisting of 100 g of carbon dioxide and 100 g of ethylene oxide. The increase in weight was 13 g.

COMPARISON EXAMPLE 2

Example 14 was repeated, only 5 g of zinc chloride being used instead of the catalyst mixture of tetrabutylammonium iodide and zinc chloride. The gas treatment was carried out using a gas mixture of 100 g of carbon dioxide and 100 g of ethylene oxide. The increase in weight was 12 g.

EXAMPLE 15a

Example 14 was repeated, the catalyst used being 2.5 g of potassium iodide and 0.65 g of zinc chloride. The gas treatment was carried out at 80° for 4 h using a total of 170 g of carbon dioxide and 120 g of ethylene oxide. The increase in weight was 130 g. If this experiment was repeated at 95°, the increase in weight over a period of 4 h was 151 g.

EXAMPLE 15b

Example 14 was repeated, the catalyst used being 2.5 g of potassium iodide and 0.19 g of zinc chloride. The gas treatment was carried out at 150° C. After 4 h, the increase in weight of ethylene glycol carbonate was 183 g.

EXAMPLE 16

A mixture of 21 g of the product from Example 14, which still contained the catalyst, and 79 g of methanol were stirred at 60°. The transesterification of the mixture was monitored by gas chromatography:

| Time (h) | Dimethyl carbonate (% by weight) | Ethylene glycol carbonate (% by weight) |
| --- | --- | --- |
| 0 | 0 | 21.2 |
| 3 | 5.1 | 10.2 |
| 6 | 8.2 | 7.5 |

Even without heating the above mixture, a substantial transesterification of the glycol carbonate to dimethyl carbonate was already found after 24 h at room temperature:

| Time (h) | Dimethyl carbonate (% by weight) | Ethylene glycol carbonate (% by weight) |
| --- | --- | --- |
| 0 | 0 | 21.2 |
| 24 | 11.6 | 5.8 |

COMPARISON EXAMPLE 3-5

As in Example 16, the corresponding amount of fresh catalyst was added to 21 g of pure ethylene glycol carbonate, which, however, contained no catalyst, and 79 g of methanol and the mixture was kept at 60° C. for 6 h and analysed:

| Comparison Example | NBu$_4$I (g) | ZnCl$_2$ (g) | Dimethyl carbonate (% by wt.) | Ethylene glycol carbonate (% by wt.) |
| --- | --- | --- | --- | --- |
| 3 | 0.25 |  | 3.9 | 16.4 |
| 4 |  | 0.06 | 3.4 | 16.9 |
| 5 | 0.25 | 0.06 | 3.1 | 17.1 |

These experiments show that the catalysts which had not been involved in the ethylene glycol carbonate synthesis but are added fresh to the transesterification are substantially less effective. In Example 16, the degree of transesterification achieved with the same amount of catalyst as in Comparison Example 5 (according to conversion from Example 14) was more than twice as high.

EXAMPLE 17

A mixture of 21 g from Example 2 and 79 g of methanol was heated for 2 h at 80° under an autogenous pressure of about 2 bar. The mixture then contained 15.4% by weight of dimethyl carbonate and only 2.6% by weight of glycol carbonate.

The same result was obtained if the transesterification was carried out at 140° C.

EXAMPLES 18-22

If Example 17 was repeated using further products from Examples 3, 4, 7 and 8, 15.2 to 16.4% by weight of dimethyl carbonate and 3.3 to 2.2% by weight of glycol carbonate were obtained in the reaction mixture in every case.

EXAMPLE 23

765 g of methanol and 100 g from Example 15b were heated at 150° C. for 2 h. A reaction product containing 9.8% of dimethyl carbonate, 2.1% of glycol carbonate and 7.6% of ethylene glycol was obtained.

EXAMPLE 24

100 g of the reaction mixture from Example 14, which still contained the catalyst, were introduced rapidly under pressure into 765 g of methanol, which was heated in an autoclave to 150° C. under the autogenous pressure, and from the time of the addition samples were taken to monitor the transesterification. After 40 min at the latest, the composition of the reaction product showed no further change and it consisted of 80.5% of methanol, 10.3% of dimethyl carbonate, 1.3% of glycol carbonate and 7.9% of ethylene glycol.

We claim:
1. Process for the preparation of dialkyl carbonates from alkylene oxides, CO$_2$ and alkanols in the presence of a catalyst, characterised in that, in a first step, an alkylene oxide having 2-8 C atoms is reacted with $CO_2$ in the alkylene carbonate which is to be formed first as reaction medium, at 40°-190° C., preferably at 50°-170° C. and particularly preferentially at 60°-160° C. and a pressure below 10 bar, preferably below 8 bar, particularly preferentially below 5 bar and very particularly preferentially below 3 bar, and, in a second step, the alkylene carbonate thus formed is transesterified with a (cyclo)aliphatic $C_1-C_{10}$ monohydroxy compound, which can be substituted by $C_3-C_6$ cycloalkyl or phenyl, at 50°-160° C., preferably at 60°-150° C. and particularly preferentially at 70°-140° C., and under the autogenous pressure, both steps being carried out in the presence of a bifunctional catalyst of the formula

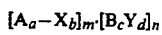

wherein
A is the cation of a metal which belongs to the
third period and Group IIa, the
fourth period and Group IIa, IVa - VIIIa, Ib or IIb, the
fifth period and Group IIa, IVa - VIIa, IIb or IVb, or the
sixth period and Group IIa - VIa of the Periodic System of the elements in the short period form,
X is the anion of an inorganic or organic acid,
B represents a cation from the group comprising the alkali metal or alkaline earth metal cations, the quaternary ammonium, phosphonium, arsonium or stibonium ions and the ternary sulphonium cations,
Y is a halide ion, preferably bromide or iodide, particularly preferentially iodide, it being possible for X and Y to change positions if at least one of the anions is bromide or iodide,
a and b independently of one another represent integers from 1 to 5 and
c and d independently of one another represent integers from 1 to 3, the requirements in respect of the valencies of the cations and anions for the formation of a neutral salt having to be met, and
m and n independently of one another assume values of 0.001-1.

2. Process according to claim 1, characterised in that an alkylene oxide of the formula

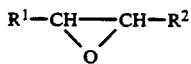

is used, wherein
$R^1$ denotes hydrogen, straight-chain or branched $C_1-C_6$ alkyl, straight-chain or branched $C_2-C_6$ alkenyl or chlorine and
$R^2$ denotes hydrogen or $C_1-C_3$ alkyl,
it being possible for $R^1$ and $R^2$ together also to represent trimethylene, tetramethylene or pentamethylene and the total number of C atoms not exceeding 8.

3. Process according to claim 2, characterised in that the alkylene oxide used is ethylene oxide, propylene oxide, 1,2- or 2,3-butylene oxide, cyclohexene oxide, vinyloxirane or epichlorohydrin, preferably ethylene oxide or propylene oxide.

4. Process according to claim 1, characterised in that A is the cation of one of the metals Mg, Ca, Sr, Ba, Zn, Cu, Mn, Co, Ni, Fe, Cr, Mo, W, Ti, Zr, Sn, Hf, V and Ta, preferably one of the metals Mg, Ca, Zn, Co, Ni, Mn, Cu and Sn.

5. Process according to claim 1, characterised in that B is a cation of the formula

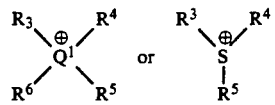

wherein
$Q^1$ represents N, P, As or Sb and
$R^3$, $R^4$, $R^5$ and $R^6$ independently of one another are straight-chain or branched $C_1-C_{18}$ alkyl or $C_7-C_{15}$ aralkyl and one of the radicals $R^3$ to $R^6$ can also be $C_6-C_{12}$ aryl,
and in that B is preferably a cation of the formula

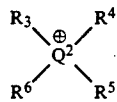

wherein
$Q^2$ represents N or P, preferably N.

6. Process according to claim 5, characterised in that the radicals $R^{13}$, $R^{14}$, $R^{15}$ and $R^{16}$, which independently of one another denote straight-chain or branched $C_1-C_{12}$ alkyl or $C_7-C_8$ aralkyl, are present in place of the radicals $R^3$, $R^4$, $R^5$ and $R^6$ respectively and one of the radicals $R^{13}-R^{16}$ can also be phenyl, and in that, preferably, the radicals $R^{23}$, $R^{24}$, $R^{25}$ and $R^{26}$, which independently of one another denote $C_1-C_8$ alkyl or benzyl, are present in place of the radicals $R^{13}$, $R^{14}$, $R^{15}$ and $R^{16}$ respectively and one of the radicals $R^{23}$ to $R^{26}$ can also be phenyl.

7. Process according to claim 1, characterised in that X assume the meaning fluoride, chloride, bromide, iodide, sulphate, nitrate, phosphate, formate, acetate, propionate, oxalate, butyrate, citrate, succinate, fumarate, maleate, benzoate, phthalate or laurate and preferably assumes the meaning chloride, bromide, iodide, acetate, laurate, nitrate or sulphate.

8. Process according to claim 1, characterised in that the aliphatic monohydroxy compounds used are straight-chain or branched $C_1-C_4$-alkanol, preferably methanol or ethanol.

9. Process according to claim 1, characterised in that the bifunctional catalyst is used in the first step in an amount of 0.005-10% by weight, preferably 0.01-5% by weight and particularly preferentially 0.02-3% by weight, based on the alkylene carbonate initially introduced, and in the second step in an amount of 0.005-5% by weight, preferably 0.01-3% by weight and particularly preferentially 0.01-1% by weight, based on the total transesterification mixture.

10. Process according to claim 1, characterised in that the bifunctional catalyst remaining in the residue after working up of the transesterification mixture which has reacted to completion is re-used in the first reaction step.

* * * * *